United States Patent [19]
Jamiolkowski et al.

[11] Patent Number: 5,681,351
[45] Date of Patent: Oct. 28, 1997

[54] SUTURE CLIP SUITABLE FOR USE ON MONOFILAMENT SUTURES

[75] Inventors: Dennis D. Jamiolkowski, Long Valley; Shawn T. Huxel, Lakehurst, both of N.J.; Daniel C. Rosenman, San Mateo, Calif.

[73] Assignee: Ethicon, Inc., Somerville, N.J.

[21] Appl. No.: 327,248

[22] Filed: Oct. 21, 1994

[51] Int. Cl.$^6$ .................................................. A61B 17/00
[52] U.S. Cl. .......................... 606/232; 606/151; 606/148; 24/136 R; 24/115 M
[58] Field of Search .................. 606/151, 157, 606/148, 139, 232, 213, 215–217; 24/136 R, 136 L, 115 M

[56] References Cited

U.S. PATENT DOCUMENTS

| | | | |
|---|---|---|---|
| 4,455,717 | 6/1984 | Gray | 24/115 M |
| 5,233,730 | 8/1993 | Milne et al. | 24/115 M |
| 5,258,015 | 11/1993 | Li et al. | 606/232 |
| 5,383,905 | 1/1995 | Golds et al. | 606/151 |

*Primary Examiner*—Jeffrey A. Schmidt
*Attorney, Agent, or Firm*—Hal Brent Woodrow

[57] ABSTRACT

The present invention provides a suture clip for attachment to at least one suture comprising a suture clip body having a central longitudinal axis, a proximal end, a distal end, an inner surface, an outer surface and a proximal surface, wherein the inner surface forms a passage that is substantially parallel to the longitudinal axis and is connected to the outer surface by a longitudinal slot which extends from the distal end to the proximal end of the suture clip body and the proximal surface has a major dimension at least five times larger than the diameter of said suture and a collar disposed about said suture clip body engaging the outer surface of the suture clip body to deflect the inner surface to frictionally engage the suture. Also described herein are methods of using this suture clip in surgical procedures.

10 Claims, 2 Drawing Sheets

SUTURE CLIP SUITABLE FOR USE ON MONOFILAMENT SUTURES

FIELD OF INVENTION

This invention relates generally to suture clips that are especially well suited for monofilament sutures.

BACKGROUND OF THE INVENTION

Surgeons in the past have tied knots in sutures by hand using a first loop and several additional throws to secure the knot. In the course of conventional surgery, this procedure would be repeated numerous times. In endoscopic surgery, where the procedure is performed through a cannula, tying knots in sutures poses a significant problem to the surgeons. Recently an alternative system of securing sutures was developed in-part to allow surgeons to quickly and easily secure the ends of a sutures during endoscopic procedures. The alternative system consists of securing at least one end of a suture, to prevent slippage, in a small clamping device referred to as a suture clip such as those described in U.S. Pat. Nos. 4,449,531 and 5,160,339. These suture clips can be easily applied with mechanical clip appliers, which are suitable for endoscopic procedures. Although these suture clip have significantly advanced securing sutures in endoscopic surgery, they are not well suited for all surgical procedures.

Suture clips generally secure one or more ends of a suture by compressing a length of the suture between two opposing surfaces. As the clip is closed on a braided suture, a short length of the suture is partially flattened by the opposing surfaces providing a better substrate for the clip to frictionally engage. Unfortunately monofilament sutures do not deform as readily as multifilament sutures.

Unlike braided sutures, monofilament sutures cannot be readily flattened between two opposing surfaces. Because of this, and the fact that monofilaments generally have very smooth surfaces, they may be significantly more difficult to frictionally grip in a conventional suture knot clip than multifilament constructions.

Compensating for the reduced frictional gripping force by increasing compressive forces exerted on the monofilament, while still utilizing conventional suture knot clip designs, requires making a much larger, bulkier, clip. Increasing the compressive force however also risks crushing the monofilament which will in turn significantly weaken the suture.

There is a second aspect of utilizing conventional suture knot clips with monofilament sutures that makes them less effective. Because monofilaments do not deform as readily as multifilaments, suture knot clips of conventional design are forced to deform more as they are being closed around a monofilament suture. The strain generated in the clip as the clip is held closed, as would be the case when the clip is in place in the body, would be correspondingly higher in the case of a monofilament suture. These high strains can cause the clip to fail prematurely with undo surgical consequences. This is especially true of clips of conventional design, made from absorbable materials, and intended to slowly loose strength as the wound heals; increased strain on the clip can cause the clip to have an increased rate of mechanical property loss causing the clip to fail much earlier than is desired.

Thus, it is an object of the present invention to provide a clip which is designed to secure sutures, but is especially adapted to secure monofilament sutures. It is a further object of the present invention to provide a suture clip that retains monofilament sutures without weakening the suture.

Other aspects and objects of this invention will become apparent hereinafter as the invention is more fully described in the following Summary of the Invention and Detailed Description of the Invention.

SUMMARY OF THE INVENTION

In accordance with the present invention, we have discovered a suture clip for anchoring at least one suture comprising a suture clip body having a central longitudinal axis, a proximal end, a distal end, an inner surface, an outer surface and a proximal surface, wherein the inner surface forms a passage that is substantially parallel to the longitudinal axis and is connected to the outer surface by a longitudinal slot which extends from the distal end to the proximal end of the suture clip body and the proximal surface has a major dimension at least five times larger than the diameter of said suture; a collar disposed about said suture clip body engaging the outer surface of the suture clip body to deflect the inner surface to reduce the size of the passage.

In accordance with another embodiment of the present invention, we have also discovered a method for anchoring a suture comprising placing a suture in a suture clip body having a central longitudinal axis, an inner surface, an outer surface, and a longitudinal slot, then securing said suture in the suture clip body by engaging a collar about said suture clip body, which engages the outer surface of the suture clip body to deflect the inner surface towards the suture, thereby frictionally engaging the suture.

DETAILED DESCRIPTION OF THE INVENTION

Figure 1:
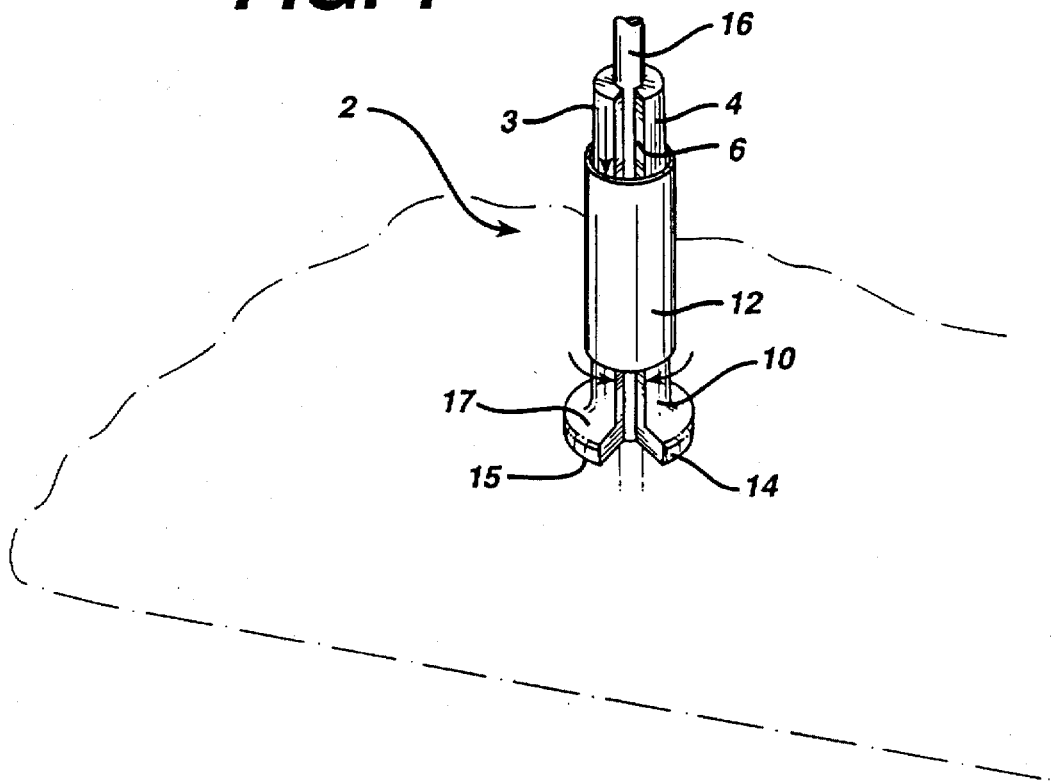
FIG. 1 is a perspective view of a first embodiment of the suture clip illustrating a suture clip body engaged about a suture by a collar. The proximal surface of the suture clip is placed against the tissue during the healing process.
Figure 2:
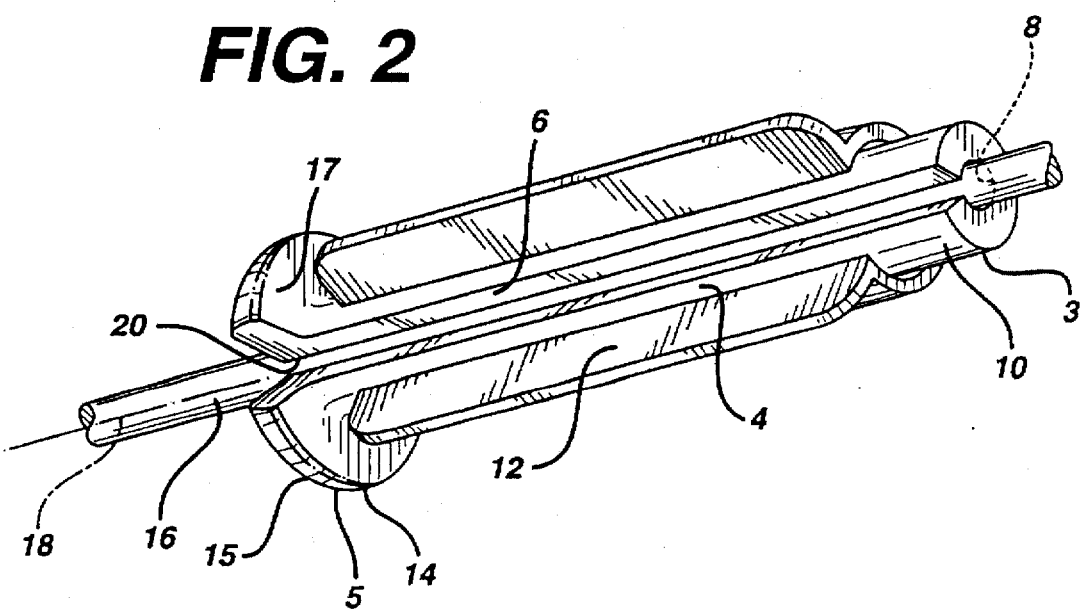
FIG. 2 is a perspective view of a second embodiment of the suture clip illustrating a suture clip body engaged about a suture by a collar.

As shown in FIG. 1 and FIG. 2, the suture clip 2 includes a suture clip body 4 and a collar 12. The suture clip body 4 has an inner surface 8 which forms a passage 20 along the longitudinal axis 18 of the suture clip body 4. The inner surface 8 of the suture clip body 4 is connected to the outer surface 10 by slot 6 which runs from the proximal end 5 to the distal end 3 of the suture clip body 4. The slot 6 allows the dimensions of the passage 20 to be reduced by the application of pressure to the outer surface 10 of the suture clip body 4. Slot 6 may also be sized to allow suture 16 to be placed within passage 20. At the proximal end 5 of the suture clip body 4 is proximal surface 15. Proximal surface 15 is provided to prevent the suture clip 2 from entering the hole in the patients tissue created by the suture needle combination.

Figure 4:
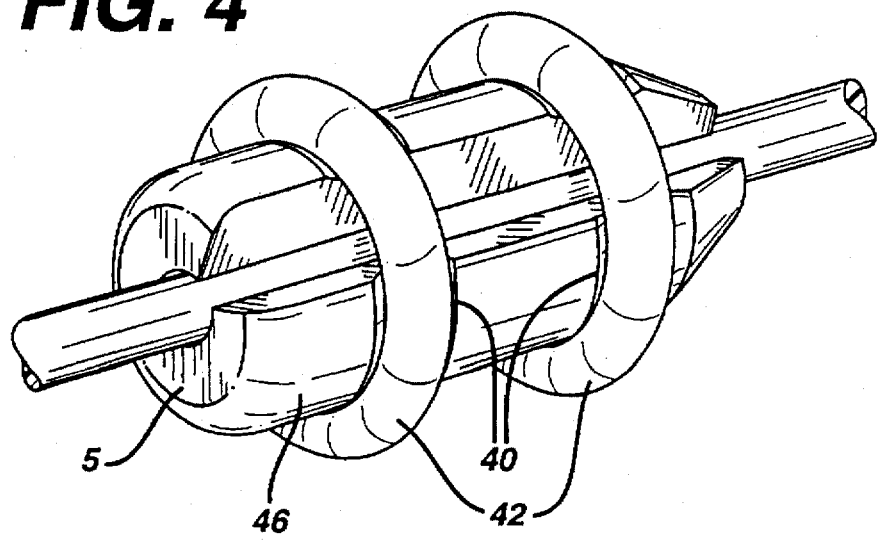
FIG. 4 is a perspective view of a fourth embodiment of the suture clip, which utilizes two collars engaged about the suture clip body in separate recessed areas.

Collar 12 is sized to engage the outer surface 10 thereby deforming the suture clip body 4 and reducing the dimensions of passage 20. The collar 12 (a sleeve) which engages around the outer surface of the suture clip body 4 as shown in FIG. 1, or the collar may be a partial cylinder engaged around the outer surface 10 as shown in FIG. 2 or a ring as shown in FIG. 4. The collar 12 maybe placed to cover slot 6 to avoid any possibility of the suture 16 slipping out of the clip via slot 6. Additionally, groves may be optionally provided in the suture clip body to aid in the placement and engagement of the collar 12 about the suture clip body 4.

The suture clip of the present invention may be constructed in various sizes according to the size suture to be secured. The suture clip body 4 will preferably have a ratio of the major dimension of the proximal surface to the suture clip's length (from its distal to proximal end) of from about 1:5 to about 1:15, most preferably about 1:10. Table I provides appropriate dimensions for suture clips with commonly employed non absorbable suture sizes.

TABLE I

| | Non-Absorbable Surgical Suture USP Requirements | | | | | | |
|---|---|---|---|---|---|---|---|
| UPS | Limits on Average Diameter (mm) | | Length of the Clip of the Present Invention* (mm) | | Major Dimension of the Proximal Surface of the Clip of the Present Invention (mm) | | |
| Size | Min | Max | Min | Max | Min | Preferred | Max |
| 8/0 | 0.04 | 0.049 | 0.20 | 25 | 0.20 | 1.9 | 15 |
| 7/0 | 0.05 | 0.069 | 0.25 | 25 | 0.25 | 2.2 | 15 |
| 6/0 | 0.07 | 0.099 | 0.35 | 25 | 0.35 | 2.7 | 15 |
| 5/0 | 0.10 | 0.149 | 0.50 | 25 | 0.50 | 3.9 | 15 |
| 4/0 | 0.15 | 0.199 | 0.75 | 25 | 0.75 | 4.5 | 15 |
| 3/0 | 0.20 | 0.249 | 1.00 | 25 | 1.00 | 5.5 | 15 |
| 2/0 | 0.30 | 0.339 | 1.50 | 25 | 1.50 | 7.4 | 15 |
| 0 | 0.35 | 0.399 | 1.75 | 25 | 1.75 | 9.5 | 15 |
| 1 | 0.40 | 0.499 | 2.00 | 25 | 2.00 | 10.0 | 15 |
| 2 | 0.50 | 0.599 | 2.50 | 25 | 2.50 | 13.0 | 15 |

*Approximately the Suture Path Length

As can be seen from Table I it is currently preferred for the proximal surface to be at least five (5) times as large as minimum diameter of the suture which is secured in the suture clip to avoid the clip being pulled into the hole left by the suture needle combination passing through the tissue. Table I also provides the preferred length from the proximal and to the distal end of the suture clip body for each suture size. Currently it is preferred that the length be at least five (5) times the minimum diameter of the suture.

As the suture clip is locked about a suture the diameter of passage 20 decreases, the inner surface 8 engages and frictionally retains the suture 16 within the suture clip body 4. Accordingly, the passage 20 of the suture clip body 4 will be appropriately sized to engage the desired size of suture 16. Additionally, to enhance the frictional force between the inner surface 8 and the suture 16, the inner surface 8 may have ridges or scoring.

In the embodiment of the suture clip 2 shown in FIG. 2, the proximal end 5 of the suture clip body 4 has projecting from the proximal end 5 outward shoulder 14. Shoulder 14 provides on one side a proximal surface 15 and on the other side a retaining surface 17. The proximal surface 15 provides a surface that contacts the tissue to being held in place by the suture 16 during the healing process. The collar 12 may be constructed so that it may be flexed and fitted over the suture clip body 4 to engage the clip about the suture.

Alternatively, the collar 12 may be slid onto the suture clip body 4 as the end of the suture is held by the surgeon the suture clip's proximal surface 15 is tight against the tissue as the collar 12 is advanced on to the clip body 4. To facilitate engaging the collar 12 about the suture clip body 4 the body can be tapered from the proximal end 5 to the distal end 3. Retaining surface 17 is positioned to stop the collar 12 from advancing beyond the proximal end 5 of the suture clip body 4.

Figure 3:
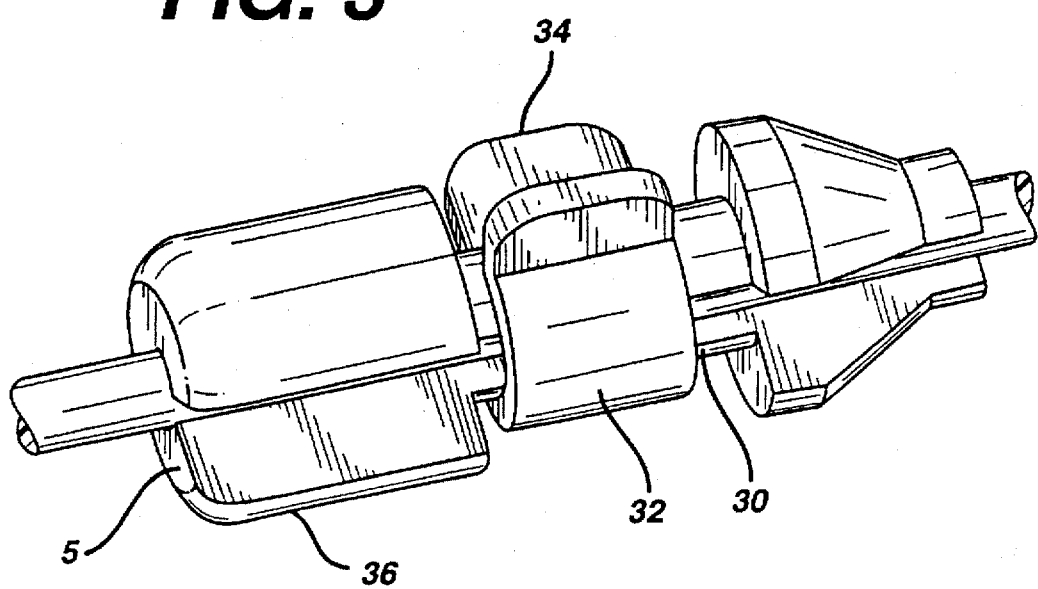
FIG. 3 is a perspective view of a third embodiment of the suture clip with a recessed area provided for retaining a collar in place about the suture clip body.

FIGS. 3 and 4 show two different embodiments of the present invention in which collar 12 is retained in recesses 30 and 40 respectively. The recess 30 shown in the suture clip body shown in FIG. 3 provides a means for securing the collar 32 such that it does not separate itself from the suture clip 34 after being engaged about the suture clip body 36. FIG. 4 provides an alternative embodiment of the present invention in which collars 42 are retained within recesses 40. The collars 42 can be one or more elastic rings that may be placed around the suture clip body 46. The recesses 40 are designed to retain the 42 in position about the surgical clip body 46.

In a surgical operation, the suture 16 would be placed in the suture clip 2 by threading it through slot 6 or through the suture clip body 4 via passage 20. The suture clip body 4 would then be positioned in the desired location and the collar 12 would be engaged about the suture clip body 4 reducing the diameter of the passage 20 thereby frictionally engaging inner surface 8 against the suture.

The clips of the present invention may be made of one or more biocompatible material using conventional fabrication methods. The clips can be composed of various biocompatible materials that will allow the suture clip body 4 to flex and contract passageway 20. Preferred are bioabsorbable polymeric materials including but are not limited to homopolymers and copolymers of ε-caprolactone, glycolide, lactide, and p-dioxanone. Preferred are non-absorbable polymers, including but not limited to, polymers selected from the group consisting of nylons, polyesters, and polypropylene. Additionally, the collars could be made from a biocompatible metal. All of these materials have been proven to be biologically acceptable when used as sutures or other implantable devices.

The preferred means for fabricating clips from polymeric materials is to injection mold a suitable polymer into an appropriately designed mold using process conditions conventionally employed for such polymer systems. After the polymer cools, the molded article can be removed from the mold and annealed or further processed before being sterilized.

The knot clips may be sterilized by any of the well known sterilization techniques. The technique selected will depend to a great extent on the material used to make the knot clip. Suitable sterilization techniques include heat or steam sterilization, radiation sterilization (such as cobalt sterilization), ethylene oxide sterilization, and other similar techniques well known in the art.

While various modifications and alternative constructions will be obvious to those skilled in the art, only a few specific preferred embodiments have been shown in the drawings and described in detail. It should be understood, however, that there is no intention to limit the invention to specific forms or examples illustrated and described. On the contrary, the intention is to cover all modifications, alternative constructions and equivalents falling within the spirit and scope of the invention as defined by the appended claims.

We claim:

1. A suture clip for attachment to at least one surgical suture having a diameter comprising:

a suture clip body having a central longitudinal axis, a proximal end, a distal end, an inner surface, an outer surface, a proximal surface, and projecting from said proximal end is a shoulder, wherein the inner surface forms a passage that is substantially parallel to the longitudinal axis and connected to the outer surface by a longitudinal slot which extends from the distal end to the proximal end of the suture clip body, the passage being suitable for placing a suture having a diameter therein, and the proximal surface has a major dimension at least five times larger than the diameter of said suture; and a collar disposed about said suture clip body engaging the outer surface of the suture clip body to deflect the inner surface of the suture clip body to reduce the size of the passage wherein the shoulder is a means for preventing the collar from traveling past the proximal end of the suture clip.

2. The suture clip of claim 1 wherein the collar consists of at least one elastic ring.

3. The suture clip of claim 1 wherein the collar is a sleeve.

4. The suture clip of claim 1 wherein the collar is a partial cylinder.

5. The suture clip of claim 1 wherein the suture clip body has a recess conformed to retain said collar.

6. A method for anchoring a suture comprising:

placing a suture in a passage within a suture clip body having a central longitudinal axis, a proximal end, a distal end, an inner surface, an outer surface, a proximal surface, and projecting from said proximal end is a shoulder, wherein the inner surface forms the passage that is substantially parallel to the longitudinal axis and connected to the outer surface by a longitudinal slot which extends from the distal end to the proximal end of the suture clip body, the passage being suitable for placing a suture having a diameter therein, and the proximal surface has a major dimension at least five times larger than the diameter of said suture; then securing said suture in the suture clip body by engaging a collar about said suture clip body, which engages the outer surface of the suture clip body to deflect the inner surface to frictionally engaging the suture wherein the shoulder is a means for preventing the collar from traveling past the proximal end of the suture clip.

7. The method of claim 6 wherein the collar consists of at least one elastic ring.

8. The method of claim 6 wherein the collar is a sleeve.

9. The method of claim 6 wherein the collar is a partial cylinder.

10. The method of claim 6 wherein the suture clip body has a recess conformed to retain said collar.

* * * * *